United States Patent
Schimpl et al.

(10) Patent No.: US 9,645,048 B2
(45) Date of Patent: May 9, 2017

(54) METHOD AND DEVICE FOR ANALYZING THE EXHAUST GAS OF INTERNAL COMBUSTION ENGINES, AND EXHAUST GAS COOLER FOR THIS DEVICE

(75) Inventors: Thomas Schimpl, Leibnitz (AT); Manuel Unger, Stainz (AT); Volker Pointner, Graz (AT)

(73) Assignee: AVL List GmbH, Graz (AT)

( * ) Notice: Subject to any disclaimer, the term of this patent is extended or adjusted under 35 U.S.C. 154(b) by 571 days.

(21) Appl. No.: 13/489,501

(22) Filed: Jun. 6, 2012

(65) Prior Publication Data

US 2012/0312075 A1    Dec. 13, 2012

(30) Foreign Application Priority Data

Jun. 10, 2011 (AT) .................................. 0863/2011

(51) Int. Cl.
*G01M 15/10* (2006.01)
*G01N 33/00* (2006.01)

(52) U.S. Cl.
CPC ....... *G01M 15/102* (2013.01); *G01N 33/0016* (2013.01); *G01N 33/0037* (2013.01)

(58) Field of Classification Search
CPC ......... F01N 3/02; F01N 11/007; G01N 33/00; G01N 33/0016; G01N 33/0037; G01M 15/10; G01M 15/102
USPC ..... 73/114.69, 114.71, 23.32, 23.31; 60/274; 123/568.12
See application file for complete search history.

(56) References Cited

U.S. PATENT DOCUMENTS

| | | | |
|---|---|---|---|
| 5,557,923 A * | 9/1996 | Bolt et al. ........................ | 60/274 |
| 2004/0006978 A1* | 1/2004 | Beck et al. ..................... | 60/289 |
| 2008/0167791 A1* | 7/2008 | Fulton et al. ................. | 701/108 |
| 2009/0101122 A1* | 4/2009 | Kurtz et al. ............ | 123/568.12 |
| 2009/0223219 A1* | 9/2009 | Joergl et al. .................... | 60/602 |
| 2013/0118232 A1* | 5/2013 | Auckenthaler et al. ..... | 73/29.02 |

OTHER PUBLICATIONS

Non-Patent Literature Nitrogen Dioxide, http://web.archive.org/web/2003072175754/http://www.oehha.ca.gov/air/acute_rels/pdf/10102440A.pdf, accessed on Jan. 17, 2015, archived on Jul. 27, 2003.*

* cited by examiner

*Primary Examiner* — Laura Martin
*Assistant Examiner* — Irving A Campbell
(74) *Attorney, Agent, or Firm* — Dykema Gossett PLLC

(57) ABSTRACT

A method for analyzing the exhaust gas of internal combustion engines provides for the cooling of the exhaust gas before analysis, the determination of the concentration of at least two different exhaust gas components in at least two separate analysis stages or the determination of the concentration of a single exhaust gas component with at least two different cooling stages. In order to achieve a higher measuring accuracy, at least one first cooling is carried out before a first analysis stage and at least one second cooling is carried out at a lower temperature than that of the first cooling before at least one further analysis stage.

7 Claims, 2 Drawing Sheets

Figure 1:
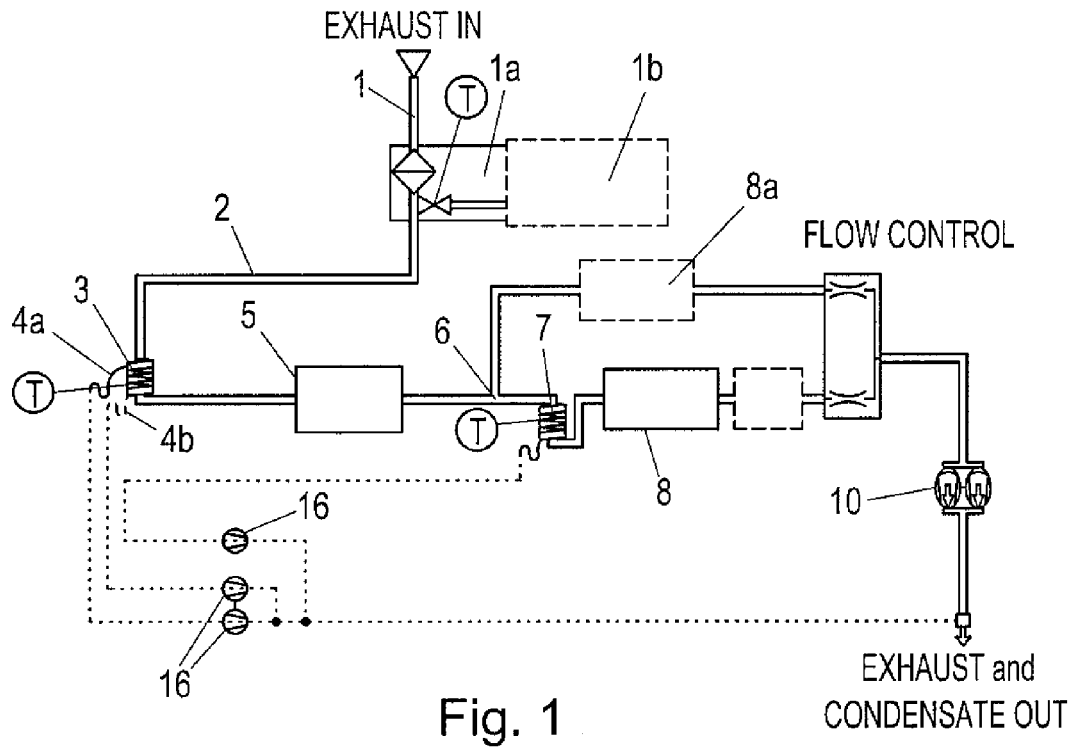

METHOD AND DEVICE FOR ANALYZING THE EXHAUST GAS OF INTERNAL COMBUSTION ENGINES, AND EXHAUST GAS COOLER FOR THIS DEVICE

BACKGROUND OF THE INVENTION

Field of the Invention

The invention relates to a method for analyzing the exhaust gas of internal combustion engines which includes the cooling of the exhaust gas before analysis, the determination of the concentration of at least two different exhaust gas components in at least two separate analysis stages, or the determination of the concentration of a single exhaust gas component with at least two different cooling stages. The invention also relates to an exhaust gas cooler for a device for analyzing the exhaust gas of internal combustion engines, as well as a device for analyzing the exhaust gases of internal combustion engines that includes at least one cooler for the exhaust gas and an analyzer arrangement for determining the concentration of at least two different exhaust gas components in at least two separate analysis stages, or for determining the concentration of a single exhaust gas component with at least two different cooling stages.

The Prior Art

In order to measure exhaust gases of internal combustion engines, appropriate preparation of the exhaust gas is necessary. The state of the art here is hot measurement of exhaust gas or cold measurement via a gas cooler. When the exhaust gas is measured cold, then it is necessary to remove water vapor. In known devices, a cooler which cools the exhaust gas to a temperature between 5° C. and 10° C. is used for this purpose. This ensures that the water content in the exhaust gas does not affect the measurement, and prevents water and hydrocarbons with higher boiling points from condensing in the analyzers. The boiling point of the exhaust gas component nitrogen dioxide which is relevant to the measurement is 21.15° C.; further, in contrast to the other exhaust gas components, nitrogen dioxide has a higher solubility in the water which condenses in the gas cooler. Both lead to a loss of nitrogen dioxide in the gas cooler and therefore to a lower concentration in the analyzer.

The object of the present invention was therefore an improvement of the method and the device for analyzing the exhaust gas with which a higher measuring accuracy is guaranteed. A further object was the design of an exhaust gas cooler which enables more effective cooling of the exhaust gas.

SUMMARY OF THE INVENTION

In order to achieve this object, according to the invention, the method specified in the introduction is characterized in that at least one first cooling is carried out before a first analysis stage and at least one second cooling is carried out at a lower temperature than that of the first cooling before at least one further analysis stage.

Advantageously, a pre-cooling of the exhaust gas is additionally carried out before the first cooling.

According to an advantageous embodiment of the invention, the first cooling is carried out at an exhaust gas temperature just above the dew point of the exhaust gas component to be determined, preferably at a temperature of between 20 and 35° C. So, for example, a cooler temperature which lies above the boiling point of nitrogen dioxide and therefore reduces the loss of nitrogen dioxide is chosen for the nitrogen oxide measurement.

A further preferred embodiment provides that a further cooling to an exhaust gas temperature between 0 and 20° C., preferably between approx. 5 and 10° C., is carried out so that the effect of water vapor on the measurement is to be minimized.

Expediently, as an additional feature, at least one condensate separation, preferably two separate condensate separations, can be carried out at each cooling stage.

In order to be able to take into account the quantities flowing through the analyzers used, a further advantageous embodiment of the invention is characterized in that the exhaust gas stream is divided before at least one of the further cooling stages, wherein only a partial stream is fed to the further cooling stage and subsequently analyzed.

Alternatively, a variant in which the exhaust gas stream is divided into at least two partial streams before at least one further cooling stage can be provided, wherein only one partial stream is fed to the further cooling stage, wherein however the concentration of at least one exhaust gas component is determined in at least two partial streams.

A further variant is characterized in that only one partial stream is cooled further after each division of the gas stream and the concentration of at least one exhaust gas component is determined in at least two partial streams.

In order to guarantee an optimum and efficient cooling for the exhaust gas when it is treated in accordance with the method described above, according to the invention, the exhaust gas cooler is characterized in that at least two coolers which are operated at different temperatures are accommodated as a combination cooler in a common, preferably insulated housing. The arrangement of the two coolers in the module allows mutual cooling and therefore a minimization of the cooling losses.

Advantageously, at least one separate condensate separation is provided for each cooling stage.

An advantageous embodiment of the cooler according to the invention is characterized in that at least one take-off for at least one partial stream is provided for at least one cooling stage.

According to the invention, for achieving the set object, the device described in the introduction is characterized in that a first cooler is connected upstream of at least one of the analyzers, and a second further cooler, which is operated at a lower temperature than that of the first cooler, is connected upstream of at least one analyzer.

According to an advantageous embodiment of the device, it is provided that the analyzer which is connected after the further cooler is a further analyzer for a further exhaust gas component.

Preferably, a pre-cooler is connected upstream of the first cooler.

According to a further embodiment according to the invention, the device is further characterized in that at least one of the coolers is provided with at least two separate condensate separators, wherein preferably a first condensate separator is arranged near the inlet of the exhaust gas into the cooler and a second condensate separator is arranged near the outlet of the exhaust gas from the cooler.

A further advantageous variant additionally provides that a branch for at least one partial stream of the exhaust gas is provided at least between one analyzer and one cooler.

If necessary, an embodiment can also be characterized in that at least one analyzer is provided for at least one cooled and at least one uncooled partial stream.

When a plurality of exhaust gas coolers is used, at least two exhaust gas coolers can be arranged in a common housing for one cooling stage in each case.

BRIEF DESCRIPTIONS OF THE DRAWINGS

In the following description, the invention is explained in more detail based on preferred exemplary embodiments and with reference to the attached drawings.

Figure 2:
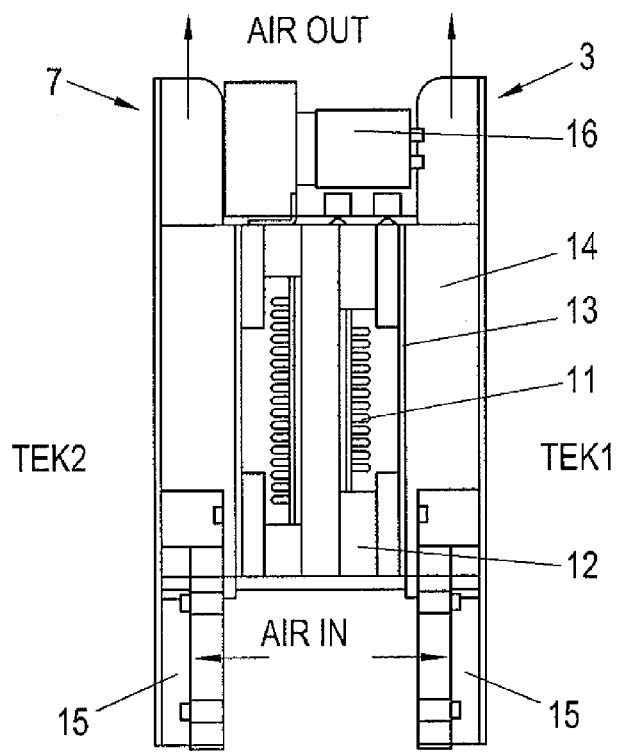
Figure 3:
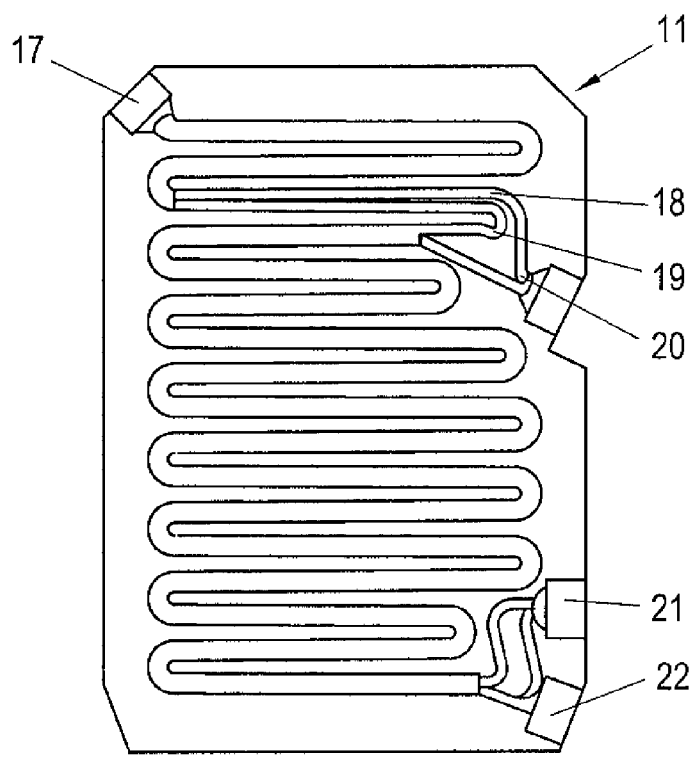
Figure 4:
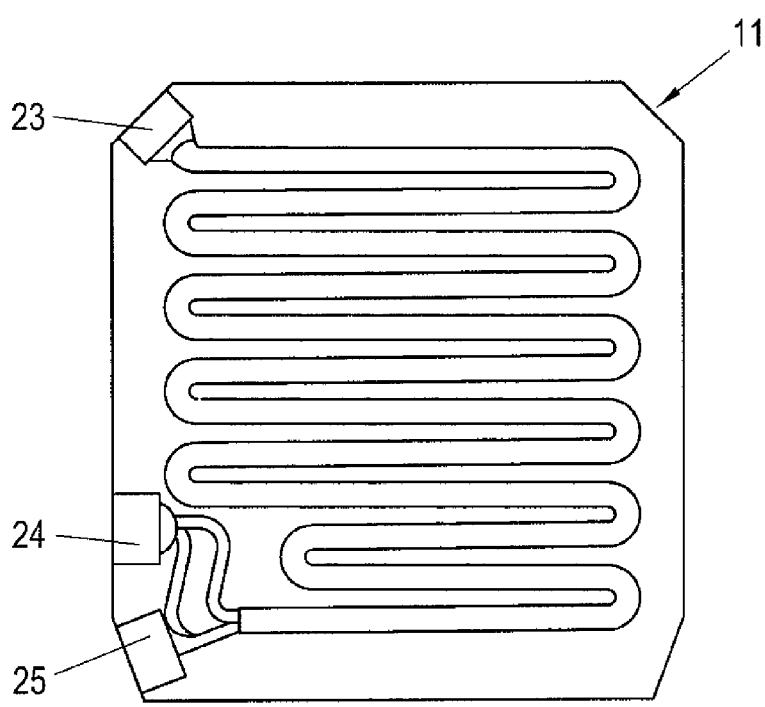

FIG. 1 shows a schematic flow diagram for the method according to the invention and the device, FIG. 2 is a plan view on an exhaust gas cooler according to the present invention, FIG. 3 is a sectional view of the exhaust gas feed in the first cooling stage of the cooler of FIG. 2, and FIG. 4 is a sectional view of the exhaust gas feed in the second cooling stage of the cooler of FIG. 2.

DETAILED DESCRIPTION OF THE PREFERRED EMBODIMENT

According to the schematic flow diagram of FIG. 1, the exhaust gas to be analyzed is fed to the device according to the invention for analyzing the exhaust gas of internal combustion engines via a heated line 1 and passes into a heated filter 1a where a particle separation and, if necessary, also particle measurement by an analyzer 1b, is carried out. The exhaust gas is fed to a first cooling stage 3 via a steel pipe 2 which effects a pre-cooling of the exhaust gas.

After the pre-cooling in the steel pipe 2, further cooling of the exhaust gas to a temperature just above the dew point of the exhaust gas component to be determined, typically to a temperature between 20 and 35° C., is carried out in the cooler of the first cooling stage 3. So, for example, a cooler temperature which lies above the boiling point of nitrogen dioxide of 21.15° C. is chosen for the nitrogen dioxide measurement, thus enabling the loss of nitrogen dioxide to be reduced.

Advantageously, two condensate separations are carried out in the first cooling stage 3 by means of condensate separators 4a, 4b.

The nitrogen monoxide/nitrogen dioxide analysis is carried out in a subsequent first analyzer 5, wherein the analyzer 5 is preferably operated at least 10° C. above the dew point of the upstream cooler.

After leaving the analyzer 5, the exhaust gas then passes to a crossing point 6 where the exhaust gas stream is divided. One of the partial streams passes into a further cooling stage 7 and subsequently into at least one further analyzer 8. The quantity of the partial stream fed to the analyzer 8 is matched to the quantity required by this analyzer 8 or by the analyzer group through which the cooled partial stream flows. The remaining portion of the exhaust gas stream bypasses the analyzer 8 uncooled as a second partial stream and is preferably recombined with the partial stream emerging from the analyzer 8, if necessary after a flow monitoring device.

Alternatively, a variant in which the exhaust gas stream is again divided into at least two partial streams before the further cooling stage 7 and only one partial stream is fed to the further cooling stage 7 could be provided, wherein however, in both partial streams, the concentration of at least one exhaust gas component, possibly the same exhaust gas component, is determined by analyzers 8, 8a or analyzer groups connected in parallel. A further variant could also provide that only one partial stream is cooled further after each division of the gas stream and the concentration of at least one exhaust gas component is determined in at least two partial streams.

The carbon monoxide/carbon dioxide content of the exhaust gas, for example, is determined in the further analyzer 8, and for this case the exhaust gas is cooled in the further cooling stage 7 to a temperature preferably between approx. 5 and 10° C., as a result of which the effect of water vapor on the measurement can be minimized. This enables a correction for the water vapor cross-sensitivity to be avoided.

In the further cooling stage 7, provision is also made to condense the water content still contained in the exhaust gas and to discharge it from the cooling stage 7 by means of a condensate separator 9.

The exhaust gas is sucked through the device by means of a pump 10 and discharged once more after the last analyzer 8 or 8a respectively.

As is shown in FIG. 2, the two cooling stages 3, 7 of FIG. 1 are formed by two coolers with gas cooling elements 11 which are operated at different temperatures and are accommodated as a combination cooler in a common, preferably insulated housing 12 for optimum and efficient cooling. The coolers are brought to the required temperature by means of Peltier elements 13. Aluminum, which is hard-coated and the hard-coated layer subsequently compacted, could advantageously be used as the base material. Glass, stainless steel and PTFE could also be used as base materials. Each cooling stage is provided with a further cooling element 14 which in each case is supplied by a fan 15. A condensate pump 16 per cooling stage 3, 7 provides for the discharge of the condensate from the cooling elements 11, wherein at least one separate condensate separation is provided for each cooling element 11.

FIG. 3 shows the exhaust gas feed in the cooling element 11 of the first cooling stage 3, in which the condensate is separated at two points. From an exhaust gas inlet 17, the gas stream passes to an extension 18 of the gas channel in order to slow down the flow speed, which prevents drops being carried along with the exhaust gas stream instead of being separated. A drip nozzle 19 serves to better hold back and separate the water drops, which are then extracted by a condensate pump 16 via the first condensate outlet 20. This prevents water which has already liquefied before and within the cooler having to be carried over the whole cooling path, which reduces NO2 losses and also saves energy. After further flowing through the cooling element 11 and after passing a second separator 21 with a second condensate outlet, the exhaust gas finally reaches the exhaust gas outlet 22.

The second cooling stage 7 shown in FIG. 4, the cooling element 11 of which is accommodated in the same housing with the first cooling stage 3, likewise has an inlet 23 for the exhaust gas which now comes from a first analyzer 4. After flowing through the cooling element 11 of this cooling stage 7 and after passing the single separator 24 with condensate outlet for this stage, the exhaust gas finally reaches the exhaust gas outlet 25 and passes out of this cooling stage 7 and also out of the complete cooling module.

The invention claimed is:

1. A method for analyzing exhaust gas from an internal combustion engine comprising the steps of:
   (a) passing the exhaust gas stream containing exhaust gas components through a first cooler so as to be cooled to a temperature of between 20° and 35° C.,
   (b) passing the cooled exhaust gas stream from step (a) through a first analyzer and determining a concentration of a first component therein having a dew point below the temperature to which the cooled exhaust gas stream is cooled in step (a), (c) after step (b), passing the cooled exhaust gas stream through a second cooler so as to be further cooled to a temperature of between 0° and 20° C., and (d) passing the further cooled exhaust gas stream from step (c) through a second analyzer and determining a concentration of one of said first component and a second component in the further cooled exhaust gas stream, the cooling to 0° and 20° C. reducing the effect of water vapor in the concentration determination of step (d).

2. The method according to claim 1, including a step of pre-cooling the exhaust gas stream prior to step (a).

3. The method according to claim 1, wherein in step (a) the exhaust gas stream is cooled to a temperature above the dew point of the exhaust gas component to be determined in the first analyzer.

4. The method according to claim 1, comprising a step of collecting condensate from the exhaust gas stream during at least one of steps (a) and (c).

5. The method according to claim 1, including the steps of ($b^1$) separating a partial exhaust gas stream from the cooled exhaust gas stream from step (b), and performing steps (c) and (d) with the partial gas stream.

6. The method according to claim 5, including the step of passing the remaining gas stream from step ($b^1$) through a third analyzer and determining the concentration of one of said first component and said second component in said remaining gas stream with the third analyzer.

7. A method for analyzing exhaust gas from an internal combustion engine comprising the steps of:

(a) passing the exhaust gas stream containing exhaust gas components through a heated filter so as to separate particles from the exhaust gas, (b) passing the filtered exhaust gas stream through a first cooler so as to be cooled to a temperature of between 20° and 35° C., (c) passing the cooled exhaust gas stream from step (b) through a first analyzer and determining a concentration of a first component therein having dew point below the temperature to which the cooled exhaust gas stream is cooled in step (b), (d) after step (c), passing the cooled exhaust gas stream through a second cooler so as to be further cooled to a to temperature of between 0° and 20° C., and (e) passing the further cooled exhaust gas stream from step (d) through a second analyzer and determining a concentration of one of said first component and a second component in the further cooled exhaust gas stream, the cooling to 0° and 20° C. reducing the effect of water vapor in the concentration determination of step (e).

* * * * *